United States Patent
Wingert et al.

[11] Patent Number: 5,780,624
[45] Date of Patent: Jul. 14, 1998

[54] PREPARATION OF OXIME ETHERS

[75] Inventors: Horst Wingert, Mannheim; Michael Keil, Freinsheim, both of Germany

[73] Assignee: BASF Aktiengesellschaft, Ludwigshafen, Germany

[21] Appl. No.: 836,885

[22] PCT Filed: Nov. 21, 1995

[86] PCT No.: PCT/EP95/04580

§ 371 Date: May 20, 1997

§ 102(e) Date: May 20, 1997

[87] PCT Pub. No.: WO96/16932

PCT Pub. Date: Jun. 6, 1996

[30] Foreign Application Priority Data

Dec. 1, 1994 [DE] Germany .......... 44 42 730.1

[51] Int. Cl.$^6$ .......... C07D 291/00; C07C 229/00; C07C 59/40; C07C 233/00
[52] U.S. Cl. .......... 544/1; 560/35; 562/470; 562/471; 564/164; 564/253; 564/254; 564/255
[58] Field of Search .......... 564/164, 253, 564/254, 255, 256; 562/470, 471; 544/1

[56] References Cited

U.S. PATENT DOCUMENTS 5,354,883  10/1994  Isak et al. .......... 560/35

OTHER PUBLICATIONS

*J. Org. Chem.*, vol. 58, No. 21, 1993, pp. 5765–5770.
*ACS Symposium Series*, vol. 443, 1991, pp. 226–235.

*Primary Examiner*—Deborah C. Lambkin
*Attorney, Agent, or Firm*—Keil & Weinkauf

[57] ABSTRACT

A process for preparing oxime ethers of the general formula I

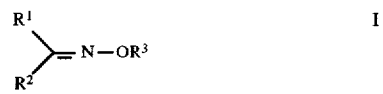

where $R^1$ is a C-organic radical, $R^2$ is hydrogen, alkoxy, cyano, nitro, $SOR^4$, $SO_2R^4$, $CO_2$-alkyl, $P(O)(OR^4)_2$ or a C-organic radical, and $R^3$ and $R^4$ are unsubstituted or substituted $C_1$–$C_6$-alkyl, entails converting an oxime of the general formula II

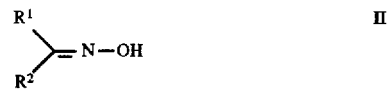

where the substituents $R^1$ and $R^2$ have the abovementioned meanings, in the presence or absence of an organic diluent, with a base into the corresponding salt, and reacting the latter with a dialkyl carbonate of the general formula III

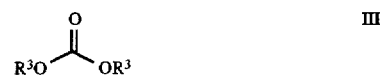

where $R^3$ has the abovementioned meanings.

13 Claims, No Drawings

PREPARATION OF OXIME ETHERS

BACKGROUND OF THE INVENTION

1. Field of the Invention

This appln. is a 371 of pct/EP95/04580 Nov. 21, 1995.

The present invention relates to a process for preparing oxime ethers of the general formula I

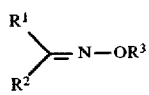

where
$R^1$ is a C-organic radical,
$R^2$ is hydrogen, alkoxy, cyano, nitro, $SOR^4$, $SO_2R^4$, $CO_2$-alkyl, $P(O)(OR^4)_2$ or a C-organic radical, and
$R^3$ and $R^4$ are unsubstituted or substituted $C_1$–$C_6$-alkyl,
which comprises converting an oxime of the general formula II

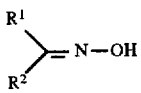

where the substituents $R^1$ and $R^2$ have the abovementioned meanings, in the presence or absence of an organic diluent, with a base into the corresponding salt, and reacting the latter with a dialkyl carbonate of the general formula III

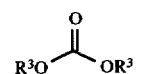

where $R^3$ has the abovementioned meanings.

The present invention preferably relates to a process for preparing oxime ethers of the general formula Ia

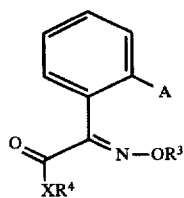

where
$R^3$, $R^4$ are, identically or differently, $C_1$–$C_6$-alkyl and $R^4$ is additionally hydrogen, and
X is oxygen and NH, and
A is the following radicals:

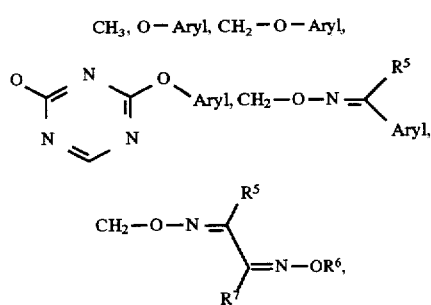

where
$R^5$–$R^7$ are, identically or differently, hydrogen, $C_1$–$C_4$-alkyl, aryl and hetaryl, with the proviso that aryl
is phenyl and naphthyl and can be substituted by from one to three of the following radicals: halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$c_1$–$C_4$-alkyl, aryl, aryloxy, benzyl, benzyloxy, hetaryl, hetaryloxy, $C_3$–$C_6$-cycloalkyl, $C_1$–$C_4$-dialkylamino, $CO_2CH_3$, $CO_2C_2H_5$, formyl and acetyl, and that
hetaryl b) by alkylation of an oxime precursor with an alkylating agent $R^1$-Z such as dialkyl sulfate or alkyl halide

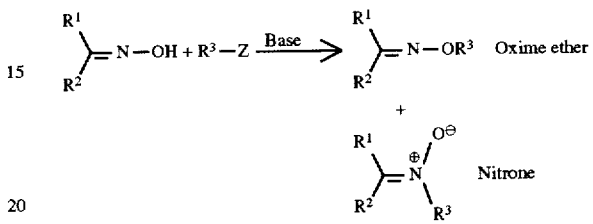

However, both process variants have considerable disadvantages which impede industrial preparation of the compounds of the general formula I. Particular mention should be made of the high price and the poor availability of alkoxyamine salts in process variant a).

The main disadvantage of variant b) is the low selectivity of the alkylation reaction; thus, besides the desired O-alkylation product, there is also obtained a 10–20% yield of the N-alkylation product in the form of the corresponding nitrone.

These two ways of preparing novel oxime ethers are described, for example, in EP-B 253 213.

EP-A 554 767 describes a process for preparing E-oxime ethers of phenylglyoxylic esters, in which E-oximes of phenylglyoxylic esters are reacted with an alkylating agent, also resulting in the corresponding nitrone, which is described in connection with procedure b), as by-product.

SUMMARY OF THE INVENTION

J. Chem. Soc. 58 (1993) 5765-70 discloses the reaction of aliphatic oximes with dimethyl carbonate to give essentially oxazolinones and only to a minor extent O-methyl derivatives. Reaction of benzophenone oxime with dimethyl carbonate resulted in 56% of the oxime methyl ether and 24% of the N-methylnitrone. Reaction of acetophenone with dimethyl carbonate resulted in 45% of the corresponding O-methyl derivative. This document shows that reaction of oximes with dimethyl carbonate has low selectivity in respect of oxime ether formation.

It is an object of the present invention to find a simple, low-cost and industrially applicable process for preparing the oxime ethers I.

We have found that this object is achieved by very selective alkylation of an oxime of the general formula II in the desired manner on the oxygen atom using a dialkyl carbonate in the presence of a base. The unwanted by-product formed by alkylation on the oxime nitrogen atom (nitrone) is produced in a maximum yield of 5% in the present process, but as a rule in a yield of <2%.

DESCRIPTION OF THE PREFERRED EMBODIMENTS

The process according to the invention is, as a rule, carried out in such a way that an oxime of the general formula II is initially reacted with a base, and the oximate which is formed is then reacted with dialkyl carbonate at 80°–130°C., preferably at the boiling point of the particular dialkyl carbonate.

It is often advantageous to isolate the oximate which is formed and then to react it in pure form with a dialkyl carbonate, preferably with dimethyl carbonate, at 80°–130° C., preferably at the boiling point of the particular dialkyl carbonate. It is preferable in this case to dispense with use of an additional solvent or diluent and, instead, employ the dialkyl carbonate in excess. The latter can be recovered during or after completion of the reaction by distillation either under reduced pressure or under atmospheric pressure.

If it is nevertheless wished to carry out the reaction in the presence of a diluent, it is appropriate to use toluene, xylene, dimethylformamide or an alcohol, such as methanol or ethanol.

The conversion of the oximes into the oximates takes place by reaction with an organic or inorganic base. Suitable organic bases are tertiary amines such as trialkylamines. Examples of trialkylamines are triethylamine, trimethylamine and diethylmethylamine.

Suitable inorganic bases are alkali metal hydroxides, carbonates, alcoholates or hydrides such as potassium carbonate, potassium hydroxide, potassium methanolate, potassium tert-butoxide, sodium carbonate, sodium hydroxide, sodium methanolate and sodium hydride. Triethylamine, sodium methanolate or potassium carbonate is preferred. The reaction of the oximes with a base is preferably carried out in the presence of a diluent such as toluene, xylene, methanol, ethanol or dimethyl carbonate. Methanol and dimethyl carbonate are preferred. This reaction is carried out at from +20° C. to +100° C. Based on oxime, from 0.1 to 3 mole equivalents of base are employed.

Dialkyl carbonates which can be employed are $C_1$–$C_6$-dialkyl carbonates such as dimethyl carbonate, diethyl carbonate, di-n-propyl carbonate, diisopropyl carbonate, di-n-butyl carbonate, di-n-pentyl carbonate and di-n-hexyl carbonate; reactions with dimethyl carbonate are, however, preferred. If an additional solvent or diluent is used, from 1 to 10 mole equivalents of dialkyl carbonate are employed. However, the dialkyl carbonate is preferably used in excess without additional diluent.

The reaction of the oximates with the dialkyl carbonates normally takes place under atmospheric pressure at 80°–130° C. However, it may be advantageous to carry out the reaction in an autoclave under a pressure of 1–100 bar, preferably in the range from 1 to 20 bar. In this pressure range, the base is preferably employed in the range from 0.1 to 1 mole equivalent, based on oxime.

The process according to the invention can be used to prepare the oxime ether of the formulae I and Ia where the substituents have the following meanings:

Alkyl represents saturated, straight-chain or branched hydrocarbon radicals with 1 to 6 carbon atoms, eg. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Halogen is fluorine, chlorine, bromine and iodine.

Haloalkyl represents straight-chain or branched alkyl groups with 1 to 4 carbon atoms such as methyl, ethyl, propyl, 1-methylethyl, butyl, 1-methylpropyl, 2-methylpropyl and 1,1-dimethylethyl, it being possible for the hydrogen atoms in these groups to be partially or completely replaced by halogen atoms, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluorethyl;

Alkoxy represents straight-chain or branched alkyl groups with 1 to 6 carbon atoms, eg. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; eg. methyl, ethyl, propyl, 1-methylethyl, butyl, 1-methylpropyl, 2-methylpropyl and 1,1-dimethylethyl which are linked to the structure via an oxygen atom (-O-);

Haloalkoxy represents straight-chain or branched haloalkyl groups with 1 to 4 carbon atoms such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl which are linked to the structure via an oxygen atom (-O-);

Alkoximinoalkyl is, for example, methoximinomethyl, 1-methoximinoethyl, ethoximinomethyl, 2-methoximinoethyl, 1-ethoximinoethyl, 2-ethoximinoethyl;

Cycloalkyl represents monocyclic alkyl groups with 3 to 12 carbon ring members, eg. $C_3$–$C_8$-cycloalkyl such as cyclopropyl, cyclobutyl, cyclopentyl, cyclohexyl, cycloheptyl and cyclooctyl;

Hetaryl or hetaryloxy represents aromatic mono and polycyclic radicals which, besides carbon ring members, can additionally contain one to four nitrogen atoms or one to three nitrogen atoms and one oxygen or one sulfur atom or no nitrogen atom and one oxygen or one sulfur atom and which are linked directly (hetaryl) or via an oxygen atom (hetaryloxy) to the structure, eg.

5-membered hetaryl containing one to three nitrogen atoms: 5-membered hetaryl groups which, besides carbon atoms, can contain one to three nitrogen atoms as ring members, eg. 3-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and one sulfur or oxygen atom or no nitrogen atom and one oxygen or one sulfur atom: 5-membered hetaryl groups which, besides carbon atoms, can contain one to four nitrogen atoms or one to three nitrogen atoms and one sulfur or oxygen atom or no nitrogen atom and one oxygen or sulfur atom, as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl;

6-membered hetaryl containing one to three or one to four nitrogen atoms: 6-membered hetaryl groups which, besides carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing one to four nitrogen atoms, 6-membered hetaryl groups in which two adjacent carbon ring members can be bridged by a buta-1,3-diene-1,4-diyl group, eg. quinoline, isoquinoline, quinazoline and quinoxaline.

The oxime ethers of the general formula I and their precursors, the oximes of the general formula II can occur as E and Z isomers. Both isomers, and E/Z isomer mixtures, are equally embraced by the application. However, the oximes of the general formula II are preferably employed as E isomers and, after reaction as claimed in claim 1, the E-oxime ethers of the general formula I are obtained.

The process according to the invention is represented by means of examples hereinafter.

EXAMPLE 1

Preparation of methyl E-2-(2-methylphenoxymethyl)phenylglyoxylate O-methyloxime.

A solution of 30 g of methyl E-2-(2-methylphenoxymethyl)phenylglyoxylate oxime [disclosed in EP 5547673][purity: 95.6%] is added to 18 g of a 30% strength methanolic solution of sodium methanolate at room temperature, and the mixture is then evaporated to dryness in a rotary evaporator at 50° C./1.33 kPa (10 mm). 100 ml of dimethyl carbonate are added and the suspension is refluxed for 11 hours. After cooling to room temperature, 200 ml of water are added, and the mixture is extracted twice with 150 ml of methylene chloride each time. The combined organic phases are dried and concentrated. The residue (29.5 g) has the following composition [% by weight quantitative HPLC analysis].

1.2% starting material (E-oxime)
0.5% methyl 2-(2-methylphenoxymethyl)phenylglyoxylate methylnitrone (nitrone)

1. A process for preparing oxime ethers of the formula Ia

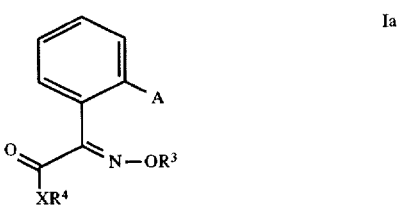

where $R^3$, $R^4$ are, identically or differently, $C_1$–$C_6$-alkyl and $R^4$ is additionally hydrogen, and X is oxygen and NH, and A is the following radicals:

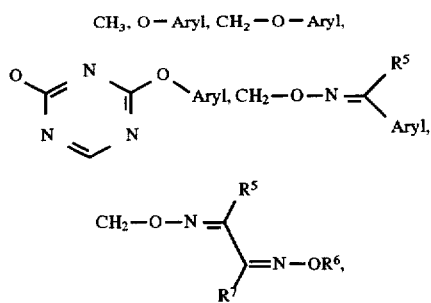

where $R^5$–$R^7$ are, identically or differently, hydrogen, $C_1$–$C_4$-alkyl, aryl and hetaryl, with the proviso that aryl is phenyl and naphthyl and can be substituted by from one to three of the following radicals: halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$–$C_4$-alkyl, aryl, aryloxy, benzyl, benzyloxy, hetaryl, hetaryloxy, $C_3$–$C_6$-cycloalkyl, $C_1$–$C_4$-dialkylamino, $CO_2CH_3$, $CO_2C_2H_5$, formyl and acetyl, and that hetaryl is an unsubstituted or substituted aromatic five or six-membered heterocycle, which comprises converting an oxime of the formula IIa

TABLE

Comparison: E-Oxime alkylation with methyl chloride/dimethyl carbonate

| | | | | | HPLC content | | |
| | Base | Solvent | Alkylating agent | Final weight | E-Oxime ether | Nitrone | O/N ratio |
|---|---|---|---|---|---|---|---|
| EP 554 767 | 29.9 g (0.1 mol) E-oxime | NaOMe | NMP | MeCl | 29.0 g | 85% | 11% | 7.7 |
| Example 1 | 30.0 g (0.097 mol) E-oxime | NaOMe | — | DMC | 29.5 g | 88.7% | 0.5% | 177.4 | we claim:

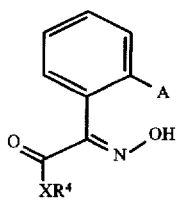

where the substituents have the abovementioned meanings, in the presence or absence of an organic diluent, with a base into the corresponding salt, and reacting the latter with a dialkyl carbonate of the formula III

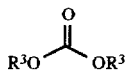

where $R^3$ has the abovementioned meanings.

2. The process of claim 1, wherein an oxime of the general formula IIb, where the substituents have the abovementioned meanings,

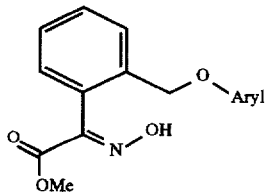

is first converted with sodium methanolate into the corresponding sodium salt, and the latter is then reacted with dimethyl carbonate to give the corresponding oxime ether.

3. The process of claim 1, wherein the compound IIc

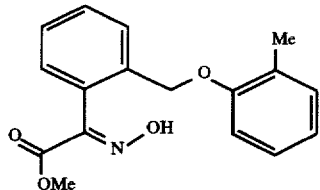

is converted with sodium methanolate into the corresponding sodium salt, and the latter is subsequently reacted with dimethyl carbonate to give the oxime ether Ib.

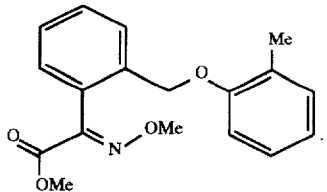

4. The process of claim 1, wherein $R^3$ and $R^4$ are methyl and X is oxygen.

5. The process of claim 1, wherein a tertiary amine or an alkali metal hydroxide, carbonate, alcoholate or hydride is used as base.

6. The process of claim 5, wherein triethylamine, trimethylamine or diethylmethylamine is used as base.

7. The process of claim 1, wherein from 0.1 to 3 mole equivalents of base are employed.

8. The process of claim 1, wherein dimethyl carbonate, diethyl carbonate, di-n-propyl carbonate, diisopropyl carbonate, di-n-butyl carbonate, di-n-pentyl carbonate or di-n-hexyl carbonate is used as dialkyl carbonate.

9. The process of claim 1, wherein the reaction of the oxime with the base is carried out at from 20 to 100° C.

10. The process of claim 1, wherein the reaction with a dialkyl carbonate is carried out at from 80 to 130° C.

11. The process of claim 1, wherein the reaction of the oxime with the base is carried out in the presence of toluene, xylene, methanol, ethanol or dimethyl carbonate.

12. The process of claim 1, wherein the reaction with a dialkyl carbonate is carried out under a pressure in the range from 1 to 100 bar.

13. The process of claim 12, wherein the reaction is carried out in the presence of from 0.1 to 1 mole equivalent of base.

* * * * *